US008546146B2

(12) United States Patent
Butler et al.

(10) Patent No.: US 8,546,146 B2
(45) **Date of Patent: *Oct. 1, 2013**

(54) PROCESS FOR EVALUATING A REFINERY FEEDSTOCK

(75) Inventors: Graham Butler, Surrey (GB); John William Couves, Buckinghamshire (GB); Paul Greenough, Buckinghamshire (GB); Nicholas John Gudde, Surrey (GB); Michael Graham Hodges, Surrey (GB)

(73) Assignee: BP Oil International Limited, Middlesex (GB)

( * ) Notice: Subject to any disclaimer, the term of this patent is extended or adjusted under 35 U.S.C. 154(b) by 237 days.

This patent is subject to a terminal disclaimer.

(21) Appl. No.: 11/662,947

(22) PCT Filed: Sep. 14, 2005

(86) PCT No.: PCT/GB2005/003560

§ 371 (c)(1), (2), (4) Date: Feb. 4, 2008

(87) PCT Pub. No.: WO2006/030218

PCT Pub. Date: Mar. 23, 2006

(65) Prior Publication Data

US 2008/0248967 A1 Oct. 9, 2008

(30) Foreign Application Priority Data

Sep. 15, 2004 (GB) .................................. 0420561.3
Dec. 15, 2004 (GB) .................................. 0427452.8

(51) Int. Cl.
*C40B 30/10* (2006.01)
*C40B 30/00* (2006.01)

(52) U.S. Cl.
USPC ................ 436/139; 436/161; 506/7; 506/12; 250/252.1

(58) Field of Classification Search
USPC ............ 436/139, 161; 506/7, 12; 250/252.1
See application file for complete search history.

(56) References Cited

U.S. PATENT DOCUMENTS

| | | | | |
|---|---|---|---|---|
| 4,534,207 | A | 8/1985 | Szakasits et al. | |
| 4,971,915 | A * | 11/1990 | Schwartz et al. | 436/139 |
| 5,600,134 | A * | 2/1997 | Ashe et al. | 250/252.1 |
| 5,699,270 | A | 12/1997 | Ashe et al. | |
| 5,774,381 | A | 6/1998 | Meier | |
| 5,895,506 | A | 4/1999 | Cook et al. | |
| 6,551,832 | B1 | 4/2003 | Deves et al. | |
| 2002/0006667 | A1 | 1/2002 | Chimenti et al. | |
| 2003/0203500 | A1 | 10/2003 | Carlson et al. | |

FOREIGN PATENT DOCUMENTS

| | | | |
|---|---|---|---|
| JP | H 11-509312 | A | 8/1999 |
| SU | 76950 | | 10/1949 |
| SU | 1029830 | A3 | 7/1983 |
| WO | WO 97/01183 | A1 | 1/1997 |
| WO | WO 01/51589 | A1 | 7/2001 |
| WO | WO 03/014264 | A1 | 2/2003 |
| WO | WO 2004/010347 | A2 | 1/2004 |
| WO | WO 2005/044961 | A2 | 5/2005 |

OTHER PUBLICATIONS

Shixioin, L., "Petroleum Refining Engineering"; *Industry Press*; pp. 168-171 (2000).

* cited by examiner

*Primary Examiner* — Krishnan S Menon
*Assistant Examiner* — Rebecca M Fritchman
(74) *Attorney, Agent, or Firm* — Nixon & Vanderhye

(57) ABSTRACT

Process for evaluating a plurality of refinery feedstocks, by providing an array of refinery feedstocks, the array having at least a plurality of different refinery feedstocks, and fractionating each of the refinery feedstocks in the array, either in parallel or in a rapid serial fashion, to produce a further array having a plurality of fractions with different chemical and/or physical properties, each fraction being representative of a process stream that might be present in a refinery. Each of the plurality of fractions is analyzed to determine one or more chemical and/or physical properties of the fractions, the analyzes being performed at least partially in parallel.

20 Claims, No Drawings

PROCESS FOR EVALUATING A REFINERY FEEDSTOCK

This application is the U.S. National Phase of International Application PCT/GB2005/003560, filed 14 Sep. 2005, which designated the U.S. PCT/GB2005/003560 and claims priority to British Application No. 0420561.3 filed 15 Sep. 2004, and British Application No. 0427452.8 filed 15 Dec. 2004. The entire content of these applications are incorporated herein by reference.

This invention relates to processes for the evaluation of refinery feedstocks and other multi-component fluids using high throughput experimentation.

Combinatorial or high throughput chemistry has revolutionized the process of drug discovery. See, for example, 29 *Acc. Chem. Res.* 1-170 (1996); 97 *Chem. Rev.* 349-509 (1997); S. Borman, *Chem. Eng. News* 43-62 (Feb. 24, 1997); A. M. Thayer, *Chem. Eng. News* 57-64 (Feb. 12, 1996); N. Terret, 1 *Drug Discovery Today* 402 (1996)). Over recent years, a number of high throughput experimentation techniques have been developed to allow significant increases in the ability to synthesize and test catalytic and other materials for useful properties. In general, such techniques have focussed on development of apparatus and methodologies, including the growing use of robots and computers to design experiments and to automate catalyst and materials preparation and testing, to allow rapid and reproducible testing results to be achieved on relatively small scale samples. For example, much effort has gone in to developing preparation and testing apparatus for numerous types of materials and material properties (such as described in U.S. Pat. No. 5,776,359) and for chemical reactions of interest (such as described in U.S. Pat. No. 5,959,297, U.S. Pat. No. 6,063,633 and U.S. Pat. No. 6,306,658).

In addition, high throughput techniques have been applied to many different analytical techniques, including separation techniques such as chromatography (such as described in U.S. Pat. No. 6,866,786). Also, cost of components has been used as a factor in the design of libraries or arrays (such as described in U.S. Pat. No. 6,421,612).

The high throughput technologies have generally focussed on discovery of new catalysts and materials for existing processes. We have now developed high throughput methodologies that can be applied to screening and optimisation of refinery processes.

Unblended crude oils contain a variety of non-purely hydrocarbon impurities, or "species", for example acids, sulphur compounds and nitrogen compounds. Different species cause a range of different problems in refineries. Because virtually all modern refineries use feedstocks which are blends of different crudes, rather than pure crudes, the effect of the varying species in the crudes can be difficult to predict and to manage. This is because once the feedstock is blended, a particular species may migrate to a different fraction (i.e. a particular "cut" of the feedstock having a particular boiling point range). An understanding of the distribution of the various species would provide extremely useful operating information for the refinery. Such information (generally known as "speciation") is, however, extremely difficult and time-consuming to obtain by traditional methods and therefore in practice, analysis tends to be restricted to analysis of unblended crude oils. From this data, attempts are made to predict the outcome of using a particular feedstock. Such predictions are however, necessarily of limited quality.

A method has now been found whereby large quantities of speciation data can be obtained and manipulated in a short period of time, allowing much better control of refinery conditions.

Traditionally, crude oil has been fractionated by distillation, and a particular species analysed in both the individual fractions and the whole crude. The resulting measurement gives an estimate of the total quantity of the species being measured; for example, for acid species, a measurement of total acidity will be obtained. If desired, further measurements can then be carried out on one or more sub-fractions. However, traditional measurements take a long time and use complex equipment. The present invention allows analysis to be carried out on a multiplicity of fractions or sub-fractions, typically all relevant fractions or sub-fractions.

Thus, according to a first aspect of the present invention there is provided a process for evaluating a refinery feedstock, said process comprising:

(i) providing a refinery feedstock;

(ii) treating said refinery feedstock to produce an array comprising a plurality of fractions having different chemical and/or physical properties, each fraction being representative of a process stream that might be present in a refinery; and (iii) analysing each of said plurality of fractions to determine one or more chemical and/or physical properties of the fractions, said analyses being performed at least partially in parallel.

In a preferred embodiment of the invention, a plurality of refinery feedstocks is evaluated, each being fractionated prior to analysis of the fractions. Thus a preferred embodiment of the invention comprises a process for evaluating a plurality of refinery feedstocks, said process comprising:

(i) providing an array of refinery feedstocks, wherein said array comprises at least a plurality of different refinery feedstocks;

(ii) fractionating each of said refinery feedstocks in said array to produce a further array comprising a plurality of fractions having different chemical and/or physical properties, each fraction being representative of a process stream that might be present in a refinery; and (iii) analysing each of said plurality of fractions to determine one or more chemical and/or physical properties of the fractions, said analyses being performed at least partially in parallel.

Preferably the fractionation step (ii) is performed either in parallel or in a rapid serial fashion with a throughput of at least 50, for example at least 250, preferably at least 2000, refinery feedstocks per week. The fractionation yields at least 2, for example at least 7 or 8, fractions per fractionation.

As used herein an array means a collection of samples that have some relationship to each other. For example the relationship may be a selection of crude oils having different sulphur content or different olefin content, or it may be a series of fractions obtained from a particular feedstock. An array may for example be presented in the form of a substrate having a set of regions in which members of that array may reside. A substrate refers to a substance having a rigid or semi-rigid surface: in many embodiments, at least one surface of the substrate will be substantially flat having a desired number of physically separate regions for different materials. Examples of substrates with, for example, dimples, wells, raised regions, etched trenches, etc., include microtitre plates or glass vial lined microtitre plates. In some embodiments, the substrate itself contains wells, raised regions, etched trenches, etc., which form all or part of the regions.

The process of the invention is carried out using high throughput experimentation techniques. Analysis is carried out on a multiplicity of fractions or sub-fractions, typically all relevant fractions or sub-fractions. Typically, a plurality of wells containing a large number of samples, for example an 8×12 array containing 96 samples, is provided on a multiplate. Each of these samples may be the same or different. Further fractionation may be carried out if desired. Each fraction or sub-fraction is then analysed, for example, for size and type of molecule. The data may then be converted into a data set, for example a three dimensional data set of molecular type/molecular size/abundance, and data maps can be generated. Use of these maps allows different feedstocks to be compared and thus refinery conditions optimised. Such mapping has never before been carried out on a refinery feedstock. In effect, accurate, rapid data measurement is being harnessed to provide information on the impact a particular feedstock will have on refinery operation.

The refinery feedstock may be any suitable refinery feedstock, including a crude oil, a synthetic crude, a biocomponent, an intermediate stream, such as a residue, gas oil, vacuum gas oil, naphtha or cracked stock, and blends of one or more of said components, such as a blend of one or more crude oils or a blend of one or more crude oils with one or more synthetic crudes.

On a typical refinery, a number of different refinery feedstocks are processed, such as a number of different crude oils. The value of a feedstock will depend on the yield, composition and properties of the distillate fractions it produces at a given refinery for subsequent refinery process streams and product blend components. The refinery feedstocks are also usually blends of available feeds, and thus, it is very difficult to predict the value of a feedstock in the overall refinery process, including detailed product quality and yield. Typically, a number of assumptions are made on the basis of previous operating experience, but these can usually only provide an approximate prediction. However, there are synergistic, antagonistic and/or non-linear effects of blending refinery feedstocks that are almost impossible to model successfully.

The present invention provides a process for the evaluation of a refinery feedstock that allows the potential value of a refinery feedstock to be evaluated prior to its use, and potentially even before its purchase. As part of this evaluation, the present invention can provide a process for the evaluation of synergistic antagonistic and/or non-linear effects obtained by blending of a refinery feedstock with one or more other refinery feedstocks on a refinery process. Since refinery feedstocks are typically blends of two or more refinery feedstocks that are available to the refinery, and, as described above, the effects of blending are difficult to model, this allows the effect of blending in differing ratios to be evaluated.

The present invention can also allow the overall refinery process to be optimized for the refinery feedstock, including optimization of various process parameters, and even aid selection of the most appropriate refinery at which a feedstock should be processed where more than one option is available.

The process of the present invention may be applied to any suitable refinery process streams, such as those described, for example, in Handbook of Petroleum Refining Processes ($2^{nd}$ Edition), edited by Robert A Meyers and published by McGraw-Hill.

In step (ii) of the present invention the refinery feedstock is treated to produce a plurality of fractions having different chemical and/or physical properties, each fraction being representative of a process stream that might be present in a refinery.

By "representative of" is meant having at least some similar chemical and/or physical properties as the typical process stream (feedstock) to a refinery process. Thus, each fraction is representative of a process stream that might be present in a refinery as a feedstream to a refinery process.

For example, the plurality of fractions may have a plurality of different boiling point ranges within an overall range typical for the process stream to the equivalent process on a refinery. A fraction with the desired boiling point range may be obtained by use of a suitable separation means, such as distillation, for example, atmospheric or vacuum distillation.

Desired chemical and physical properties of the process streams (feedstocks) to particular refinery processes will depend on a particular refinery configuration, but typical properties are described, for example, in Handbook of Petroleum Refining Processes ($2^{nd}$ Edition), edited by Robert A Meyers and published by McGraw-Hill.

In one extreme, the refinery feedstock may be divided to produce a portion for each of the plurality of fractions subsequently desired, wherein each portion is treated to produce a fraction with the desired properties, such as with a desired boiling point range.

Alternatively, the refinery feedstock may be divided initially to produce 2 or more portions, and each portion treated to produce portions with desired properties. One or more of these separate portions may subsequently be further divided and treated, either chemically and/or physically to produce the required number of fractions with the desired (different) properties. Thus, where a process may be operated using process streams with a variable boiling point range in the range of 150-250° C., a first portion may be treated to produce a fraction of boiling point range 150° C. to 250° C., and a second portion may be treated to produce a fraction of boiling point range 160° C. to 230° C.

In addition to, or optionally in alternative to, any other treatments of the refinery feedstock to produce a plurality of fractions having different chemical and/or physical properties, each fraction being representative of a process stream that might be present in a refinery, the treating of the refinery feedstock to be evaluated may comprise the step of blending said refinery feedstock with one or more other refinery feedstocks, and, in particular, may include producing a plurality of fractions of differing properties by blending portions of the initial refinery feedstock with different other refinery feedstocks and/or with other refinery feedstocks in different ratios. The blended refinery feedstock may typically comprise a blend of 3 to 20 different components, such as crude oils.

In general, any suitable physical or chemical treatment method may be used to obtain the plurality of fractions having different chemical and/or physical properties, each fraction being representative of a process stream that might be present in a refinery. Suitable physical or chemical treatment methods used to obtain the plurality of fractions having different chemical and/or physical properties in step (ii) will generally be representative of equivalent processing steps that might occur in conventional refinery processes.

For example, a microdistillation column or microfractionator (representing a crude oil distillation unit in a refinery) may be used on each portion to obtain fractions with defined boiling point ranges. Other techniques may include solvent extraction, membrane treatments, adsorption treatments and suitable chemical reactions. Chemical reactions, including catalysts where appropriate, will generally be chosen that are representative of chemical reactions that might occur in conventional refinery processes.

Combinations of techniques may be required, for example, micro-distillation followed by a chemical reaction to represent crude oil distillation followed by a conventional treatment of said fraction that occurs in a refinery process. For example, one or more portions may be produced by fractionation and then may be hydrotreated (optionally under different process conditions for each portion) to represent streams which may be obtained from a hydrotreater in a refinery (and which would typically then be fed to a catalytic reforming process).

Chemical treatment of the refinery feedstock may also comprise additive treatment, for example, addition of desalting additives, corrosion passivation additives (typically used in distillation columns), anti foulants (used in various refinery processes).

The treatment conditions in step (ii) will generally be process dependent, and, where the process is a catalysed process, may also be catalyst dependent. Process conditions may include, for example, temperature, contact time/space velocity and/or total pressure or partial pressure of specific reactants, e.g. hydrogen partial pressure is a variable in hydrotreating.

The treatment in step (ii) may comprise dividing the refinery feedstock into a plurality of portions and subsequently treating each portion to produce a fraction with a boiling point range typical for a suitable fraction conventionally obtained from a crude distillation unit at a refinery. For example, the treatment in step (ii) may comprise dividing the refinery feedstock into a plurality of portions and subsequently treating each portion to produce a fraction with a boiling point range in the range of 150° C. to 250° C., which is a typical range for the kerosene fraction of crude oil, or 200° C. to 350° C., which is a typical range for the gas oil fraction of a crude oil.

It should be noted that these ranges overlap. This is one example of the usefulness of varying the boiling point range of the fractions within the overall possible range for a particular subsequent process.

The dividing may be achieved by any suitable means. For example, the dividing may be performed in a batch mode by using one or more automated syringes to provide the plurality of portions. Alternatively, a series of microflow controllers or microvalves may be used in which the flow for each portion is generally continuous, but can be started and stopped, and optionally varied, using the valve or controller. As a further alternative, a plurality of baffles or other flow control means, such as orifices in a plate, where flow can't be shut-off or varied independently for each portion, but which provide an even flow distribution across the plurality of portions, may be used.

In one embodiment, the portion is placed on a heating device, heat is then applied to increase the sample temperature, and the fraction which boils between the desired ranges is collected, for example, by using a suitable valve to collect the fraction of the correct boiling range, which is then cooled to condense said fraction. The heating device may be a heated microoscillator, as described in U.S. Pat. No. 5,661,233.

In another embodiment, each portion may be placed in an enclosed channel comprising at least three sections, each section separated by valves or other suitable barriers which liquid samples cannot pass, but gaseous samples can. Thus, each portion may be placed in the first section of a channel and the first section heated to the upper boiling point of the boiling point range desired, for example using a heating laser to give local heating, and the second section may be maintained at ambient temperature (or below), such that all material with a boiling point below the upper boiling point vaporises and passes from the first section into the second section, where it condenses.

The second section is then heated to the lower boiling point of the range desired, for example using a heating laser to give local heating, and the third section is maintained at ambient temperature (or below), wherein all material with a boiling point below the lower boiling point vaporises and passes from the second section into the third section, leaving, in the second section, a fraction with the desired boiling point range.

Alternatively, the second section may be maintained at the lower boiling point throughout, such that material with a boiling point above the range desired remains in section 1, material with a boiling point in the range desired is collected in section 2, and material with a boiling point below the range desired is collected in section 3.

A plurality of channels, each having the at least three sections may be provided on a spinning disk-type separation device as described in WO 01/87485 or WO 2004/58406.

In general, the plurality of fractions produced in step (ii) comprises at least 7 such fractions, such as at least 20 such fractions. It is a feature of the present invention that the treatment of a refinery feedstock to produce the plurality of fractions may if desired be performed at least partially, for example predominantly, preferably entirely, in a parallel manner, by which is meant that the plurality of fractions are produced in parallel, and, hence, are available to be analysed at any particular instance. In addition to the plurality of fractions having different chemical and/or physical properties produced, some "identical" fractions may also be produced (and subsequently analysed) for the purposes of ensuring/checking reproducibility.

In step (iii) each of the plurality of fractions is analysed (characterised) to determine one or more chemical and/or physical properties of the fractions. The chemical and/or physical properties of the fractions which it may be desired to analyse in step (iii) of the process of the present invention will generally be stream dependent, and may include density, specific gravity, total acid number (TAN), total base number (TBN), cold flow properties (such as pour point, freezing point and cloud point), viscosity, hydrocarbon speciation (e.g. aromatics content), sulphur content, sulphur compounds speciation, nitrogen content, nickel compounds content, acid speciation (e.g. sulphidic, naphthenic and subdivisions there of), asphaltine content, carbon content, metal content (such as nickel, vanadium, iron, calcium), micro carbon residue, chloride (content and type organic/inorganic) and combinations thereof.

Any suitable appropriate analytical technique may be used. The analyses may be performed by any suitable method, for example using a rapid analysis tool, such as fast GC, 2D GC, or mass spectrometry. The analysis of at least one chemical or physical property is suitably performed predominantly in parallel e.g. by using two or more analytical devices operating on different fractions. Preferably the fractions are analysed for at least one property in an entirely parallel fashion, by which is meant that each fraction is analysed for that property simultaneously. For example, a separate analytical device, for example a micro-GC, may be provided for analysis of each fraction. Other types of parallel analysis that may be used include multi channel or plate-based liquid chromatography and/or plate-based electrophoresis, where multiple samples can be analysed in parallel on a single plate. Chemical species may be identified on the plate by use of structurally or functionality specific chemical dye, or chemical visualisation (e.g. under UV irradiation) agents. In addition micro fluidic techniques may be applied to increase the throughput. It will be understood that multiple analyses of a fraction for different properties can be carried out in rapid serial fashion, i.e. by carrying out a set of parallel analyses for a first property, and subsequently carrying out a set of parallel analyses for a second property. Alternatively, all analyses, including those for different properties, may be carried out entirely in parallel. It is important that the analyses of step (iii) should be carried out at a rate able to match the throughput of samples from steps (i) and (ii) of the process. Preferably the properties of the fraction which are analysed include one or more chemical properties. Chemical properties can have significant influence on the value of the fraction and on its potential impact on subsequent processes to which it might be fed, including subsequent catalysed and uncatalysed refinery processes and the process operability of the refinery (corrosion or fouling).

Typical catalysed refinery processes, for example, include hydrotreating, selective hydrotreating, isomerisation, aromatic saturation, hydroisomerisation, hydrocracking, hydrogenation, catalytic cracking, combi cracking, reforming, isodewaxing, sweetening (e.g. the Merox process), dealkylation, transalkylation, etherification, OATS, catalytic dehydrogenation (e.g. the Oleflex process), $C_3$ or $C_4$ olefin dimerization (e.g. the Dimersol process), MTBE, Isal, alkylation and Octgain.

Typical uncatalysed processes in a refinery, for example, include crude oil desalting, crude oil distillation, vacuum distillation, membrane extraction, solvent extraction, thermal cracking (e.g. visbreaking), coking, coke calcining, bitumen blowing and gasification.

In one embodiment, the treatment and analysis of steps (ii) and (iii) of the process of the present invention is performed using an array of treatment steps suitable to give the plurality of fractions, for example, an array of blenders and/or and array microfractionators, and an array of suitable analysis devices, for analysis of each of the fractions. The array may be a microfabricated array, for example on a silicon wafer.

The evaluation according to the process of the present invention may be enhanced by performing further experiments repeating steps (ii) and (iii) of the present invention. Thus, whilst the refinery feedstock may be evaluated for one plurality of fractions, the overall evaluation may be enhanced by repeating steps (ii) and (iii) for one or more further pluralities of fractions of the same initial feedstock but which have been treated in a slightly different manner. For example, the first plurality of fractions may be a plurality of blends which have each been blended with different ratios of components but where each fraction is treated to have the same boiling point range, and the second plurality of fractions may comprise fractions having the same respective blending ratios but which have been treated to have a different boiling point range. As a further example, the process conditions of any chemical reactions by which the fractions have been produced in step (ii) may also be varied with time.

This allows a number of variables to be screened rapidly and controllably, and enable the optimum process conditions for each fraction in the refinery process to be determined.

Since refineries do have the ability to vary the operation, such as of a distillation column, within certain ranges to select different temperature ranges for particular cuts of a feedstock, this can enable the process of the present invention to provide information on the optimum operating conditions for the distillation column in a refinery as a function of other feedstock treatments, such as blending ratios. In this manner, synergies may be identified.

Preferably, the process of the present invention is performed in a continuous mariner, by which is meant that the treatment to produce a plurality of fractions each representative of the typical process stream for said refinery process in step (ii) and the analysis of said fractions in step (iii) is performed in an integrated and continuous, rather than a batch-type, manner. Thus, the treatment of step (ii) may comprise continuously feeding the refinery feedstock to treatment steps to produce a plurality of fractions as continuous process streams which are subsequently analysed in step (iii). This represents the processes generally occurring in a refinery more closely, and is different to typical crude oil assay testing, which is generally performed in batch tests. When the invention is performed in a continuous manner it is also possible to vary certain properties of the plurality of fractions in a continuous or semi-continuous manner, for example, to explore the effect of different blending ratios or fractionation temperature ranges in step (ii).

The process of the present invention can be repeated as necessary for different refinery feedstocks and blends thereof.

The process of the present invention can be repeated as necessary for analysis of different physical and/or chemical properties of the fractions. Thus, the fractions may be analysed to measure, for example, metals content, and subsequently the process repeated (or "continued") and analysis changed to enable measurement of, for example, sulphur content of the fractions. Alternatively, or in addition, analysis by different techniques and/or for different properties may be performed in parallel on said fractions (or on portions thereof).

The process of the present invention can be applied separately to a number of different refinery process streams. Thus, it is may be appropriate to have one or more arrays of treatment and analysis steps for producing and analysing process streams representative of those from a crude distillation unit and for subsequent hydrofining (gas oil fraction) and one or more arrays of treatment and analysis steps for producing and analysing process streams representative of those from a hydrotreating process and for subsequent catalytic reforming and/or isomerisation, and so on as required.

Alternatively, evaluation of process streams may be "linked". Thus, in a further embodiment, the process of the present invention may be applied to evaluating the refinery feedstock by analysis of two or more pluralities of different process streams.

In a first aspect of this embodiment of the present invention, the refinery feedstock may be evaluated by production and analysis of process streams that are produced "in series" on a refinery. Thus, after analysis of a plurality of fractions in step (iii) of the process of the present invention, one or more of the plurality of fractions, typically all, may be further treated to produce one or more further streams each being representative of a different (i.e. subsequent) process stream that might be present in a refinery. For example, in step (ii) of the process of the present invention fractions may be produced having properties (e.g. a boiling point range in the naphtha range) typical of that obtained from a crude distillation unit for feeding to a hydrotreater, and these streams may be analysed in step (iii). Subsequent to this, each fraction may be further treated, for example, may actually be hydrotreated, to produce streams having properties typical of those obtained from a hydrotreater for feeding to a catalytic reforming and/or an isomerisation process, and subsequently reanalysed.

In a second aspect of this embodiment of the present invention, the refinery feedstock may be evaluated by production and analysis of process streams that are produced "in parallel" on a refinery. For example, the refinery feedstock may be treated to produce a plurality of fractions each representative of a first process stream and a plurality of fractions each representative of a second process stream. An example of this aspect includes separating a refinery feedstock into a first plurality of fractions representative of kerosene fractions from a crude distillation unit (which would subsequently be passed to a sweetening process) and a second plurality of fractions representative of gas oil fractions from a crude distillation unit (and which would subsequently be passed to a hydrofining process), and analysing each of these respectively.

A combination of these first and second aspects may be used to evaluate a number of processes on a refinery simultaneously. This embodiment has the advantage that the effect of a change in one variable (in a treatment step) such that the properties of one of the first plurality of fractions is changed can be simultaneously evaluated against consequent changes in properties of one of the second plurality of fractions. A significant number, such as at least 5 process streams, for example 10 or more, may be evaluated in this "linked" way to provide information on the optimum refinery configuration for a particular feedstock. This may be achieved by providing any required treatment steps on a suitable microfabricated array or arrays.

In a preferred embodiment of the present invention, once the analysis of step (iii) has been performed, suitable refinery process models are applied to determine the impact of the chemical and/or physical properties of the fractions on the subsequent processing of the fraction/process stream or on the overall processing of the refinery feedstock. Suitable refinery models are known to the person skilled in the art, and may include, for example, linear programme models for feedstock and product evaluation, process optimisation models, such as for individual process unit optimisation and refinery-wide optimisation, and/or risk-based models, for evaluation of processing impacts of the process stream or refinery feedstock generally.

The process of the present invention will generate a large amount of data on the effect of refinery feedstocks on refinery process streams. In a further embodiment, this data may be utilised to develop, update, maintain and/or verify process models for one or more refinery processes (either individually or "linked" processes). For example, a large amount of data may be rapidly produced over a broader parameter set than from pilot plant parameter studies enabling the building of a process model, and further data generated may be utilised to provide continuous update and refinement of the process model (for example, for a wider parameter space (e.g. adding different catalysts, different compositions)).

Modelling or other experimental design techniques may be used to generate a set of variable process conditions for one or more refinery feedstocks (including blends) which it is desired to evaluate for the development, updating or verification of one or more process models, and the process of the present invention can be specifically used to evaluate the processes to generate the required data for the process models, such as yield and quality of products from the refinery feedstock or feedstocks under the defined process conditions.

In a further embodiment of the invention, there is provided a method for determining the value of a multi-component fluid, comprising i) providing a library comprising a plurality of multi-component fluids;
ii) separating each of said multi-component fluids into at least two components at the rate of at least 50 multi-component fluids per week;
iii) analyzing each of said at least two components for one or more chemical and/or physical properties; and
iv) determining a value of each of said plurality of multi-component fluids in said library.

The value of the multi-component fluid can be any one or more of a number of different items, including (i) the price of the components in the multi-component fluid in a particular industry, (ii) an optimum processability of the multi-component fluid, (iii) a type or specific processing unit or facility to accommodate the multi-component fluid, (iv) the type or specific configuration of equipment to process the multi-component fluid, (v) the type or specific configuration of processing steps to process the multi-component fluid, and/or (vi) the type or specific blending materials for the multi-component fluid (such as another multi-component fluid).

Arrays or libraries of multi-component fluids may be provided. Two or more components of the fluids are separated in a high throughput system or method to form arrays or libraries of two or more components. These component arrays or libraries are then tested in a high throughput system or method to determine composition, character or properties. These determinations are used to determine a value for the multi-component fluid in an industry.

The high throughput separation and testing can take place in a parallel or simultaneous fashion and/or in a rapid serial fashion. The throughput of the overall workflow is important, with the rate or sample of multi-component fluid per unit time varying depending on the industry in which value will be determined. For example, in the oil industry, crude oil separation and component analysis can take place at the rate of at least 50, for example at least 250, preferably 2000, different crude oil multi-component samples in 7 days. Multi-component fluids include materials such as crude oil, other refinery feedstocks, pharmaceuticals, etc.

Value determinations can be made before or after purchase of non-sample quantities of the multi-component fluids, with the value determination assisting in optimizing value extraction.

In a preferred embodiment, for measuring acid speciation, which is generally determining the species of acids in a sample, the process of the invention comprises four steps: 1) sample preparation: the acids are extracted from the multi-component sample, together with other polars in a liquid-liquid extraction, using a blend of organic and/or inorganic bases, organic solvents and water. Alternatively a simple solid phase extraction process based on silica-filled 96-well microtitre plate can be used for extraction of polars, under the conditions of flash or normal-phase chromatography; 2) first dimension separation and first property determination: the acid strength separation is performed by selective retention of the acids on a 96-well solid phase extraction plate filled with an ion exchange resin having selectivity for acids and subsequent multi-step elution using several buffers of increased acidity (various concentration of an acid in an aqueous mixture), which separates acid components in the multi-component sample by acid strength and wherein the repeated multi-step elutions provide information about the acid strength (e.g., order of elution or time of elution) that is inputted into the processing system for mapping or layout; 3) second dimension separation and second property determination: each effluent from the first dimension (i.e., component) is then separated by hydrophobicity by rapid serial or parallel high performance liquid chromatography (HPLC) with UV-Vis detection (e.g., 200-380 nm absorbance), using a reversed-phase column with a mixture of solutions used as the mobile phase (for example, water/tetrahydrofuran/cyclohexane); and 4) layout or mapping and sample characterization:

after background subtraction, the HPLC traces corresponding to individual components (e.g., solid phase extraction elutions) for each multi-component sample are recombined into a two dimensional acid distribution map (the layout), in which the x-y-z coordinates are made of the HPLC retention time, the solid phase extraction elution order and the HPLC detection signal, and optionally the HPLC traces are integrated into several zones and each peak area is converted into the acid abundance values (mgKOH/g equivalents) by multiplying with zone-specific response factors.

The following is an Example of this embodiment of the invention.

EXAMPLE

This example uses fractions of crude oil, which can be any crude oil. An array of 96 crude oil fractionated samples is provided in a substrate having 96 wells glass lined with glass vials.

Liquid-Liquid Extraction (LLE)

The samples are being targeted to be approximately 500 mg each, and each is weighed using either manual weighing or a Bohan automated weighing station. 1 ml per 500 mg of sample of a hydrocarbon solvent is added to each well and the array is mixed well on a shaker plate. The array can be heated to ensure that any solid samples are flowable. 4 ml of extractant solution is added to each vial, with the extractant solution composed of 80 parts isopropanol and 20 parts of 100M triethylamine in water. The vials are rigorously shaken for at least one hour, and then centrifuged for at least 5 minutes. An aliquot of each vial is taken from the aqueous portion of the extract solution.

First Dimension Separation

The first dimension separation is a solid phase extraction using a commercially available 96-well plate having an ion-exchange resin with high affinity for acids, specifically the Oasis MAX from Waters (60 mg of ion-exchange resin per well, 30 micron resin particle size) fitted with a Speedisk® pressure processor and manifold air pressure of 30 psi. Each well of the solid-phase extraction plate is preconditioned with isopropanol and water. The aliquot of sample from the aqueous fraction of the LLE step is loaded in steps into each well of the 96-well SPE plate, either manually with a parallel pipette or with an automated liquid handling robot. The extracts are pushed through the SPE plate slowly with no or minimum pressure applied. After loading is completed, isopropanol followed by a mixture of isopropanol and water are pushed slowly through the SPE under the same conditions. Elution is performed in parallel for all 96 wells and in stages starting with the weakest acidic eluent and ending with the strongest acidic eluent. In this example, there are four elusions. In the first elution, 0.5 mL of 0.178 M formic acid is loaded onto each well and pushed through at the pressure adjusted to maintain a steady flow of about 0.1 mL/min across the plate. Up to 0.5 mL of the effluent is collected into a separate 96-well microtiter plate and cooled. In the second elution, 0.5 mL of 0.356 M formic acid is loaded onto each well and pushed through at the pressure adjusted to maintain the same flow. Again, up to 0.5 mL of the effluent is collected into a separate 96-well microtiter plate, and cooled. In the third elution, 0.5 mL of 0.890 M formic acid is loaded onto each well in four equal portions and pushed through at the pressure adjusted to maintain the same flow rate. Again, up to 0.5 mL of the effluent is collected into a separate 96-well microtiter plate, and cooled. In the fourth elution, 0.5 mL of 1.425 M formic acid is loaded onto each well in four equal portions and pushed through at the pressure adjusted to maintain the same flow rate. Again, up to 0.5 mL of the effluent is collected into a separate 96-well microtiter plate, and cooled. The order of elution is recorded by coding each sample with a sample name that reflects its order of elution (e.g., using a processing system readable bar code).

Second Dimension Separation

The four plates with effluents from the anion-exchange separation are put on the platform of a robotic liquid handling robot associated with a parallel capillary HPLC device, equipped with a UV-vis absorbance detector at the end of each of eight columns. Specifically, an 8-channel capillary HPLC ExpressLC™-800 from Eksigent, with robotic autosampler HTS Pal from CTC Analytics/Leap Technologies is useful. There is an injection port and a sample valve holding two sample loops for each column, and each column is a reverse-phase column packed with 3.5 micron octyl-silica particles. Commercially available software runs the robot for injection, pumping and data collection from the detector. A gradient elution is used starting with a MobilePhase-A and moving to MobilePhase-B. MobilePhase-A is a mixture of 4 ingredients, including a majority of water and THF and a minority of two hydrocarbon solvents. MobilePhase-B is a mixture of 4 ingredients, including a minority of water and THF and a majority of two hydrocarbon solvents.

An aliquot of each of the effluent sample is injected onto the mobile phase of a capillary HPLC column. After injection a gradient elution program is executed, starting with 26 μL/min of 25 equivalents of MobilePhase-A and 1 equivalent of MobilePhase-B and holding it for about 15 seconds, followed by changing the mobile phase flow rate and composition to 37 μL/min of 1 equivalent of MobilePhase-A and 35 equivalents of MobilePhase-B in about 90 seconds, holding that composition for about 3 min, and subsequently returning back to original flow rate and composition. Each sample can take about 5 minutes, with 8 samples being run simultaneously, requiring about 1 hour per plate or all 384 samples in 4 hours. In addition, the robotic autosampler fills the injection loop with solvent between samples to clean the column between samples. Each HPLC separation produces a trace of time vs. detector response at UV-Vis absorbance wavelengths in the range of 200-380 nm.

Data Reduction and Mapping

For each HPLC trace, a 10 nm bandwidth is extracted from the raw data at an appropriate wavelength and baseline-corrected using the signal at 530 nm at 50 nm bandwidth. Background profiles are prepared by performing both first and second dimension separations as discussed above using samples that contain no fractioned crude oil. These background profiles are then extracted from each individual sample trace. The four background-extracted traces per fractionated crude oil sample, representing the order of elution from the first dimension, are re-composed into two dimensional maps in which the HPLC elution time makes X-axis, the order of the SPE elution makes the Y-axis, and the HPLC detector response makes the Z-axis. The background-extracted traces are also integrated into three zones of elution times, yielding peak areas per zone. The peak areas are then multiplied by the zone-specific response factors, yielding the acidity abundance values per each zone in equivalents of mg KOH per g of fractionated crude oil sample. The acidity abundance values for each zone (4 SPE effluents×3 HPLC elution time ranges) are summed together, yielding the total acidity value of petroleum sample, which can then compared to the TAN of the crude oil sample prepared by ASTM standards.

The invention claimed is:

1. A process for evaluating a plurality of refinery feedstocks, said process comprising the steps of:

(i) providing an array of refinery feedstocks, wherein said array comprises at least a plurality of different refinery feedstocks;

(ii) fractionating each of said refinery feedstocks in said array in parallel to produce a further array comprising a plurality of fractions having different chemical and/or physical properties, each fraction being representative of a process stream that might be present in a refinery, wherein the fractionation step comprises treating each feedstock or a portion thereof using a microdistillation column or microfractionator to obtain fractions with defined boiling point ranges; and (iii) analysing each of said plurality of fractions to determine one or more chemical and/or physical properties of the fractions selected from density, specific gravity, total acid number, total base number, cold flow properties, viscosity, hydrocarbon speciation, sulphur content, sulphur compounds speciation, nitrogen content, nickel content, vanadium content, acid speciation, asphaltine content, carbon content, metal content, micro carbon residue, chloride, and combinations thereof, said analyses being performed at least partially in parallel.

2. A process as claimed in claim 1, wherein the fractionation step (ii) is performed with a throughput of at least 50 refinery feedstocks per week.

3. A process as claimed in claim 1, wherein in step (iii), analysis of each fraction for a first property is carried out in parallel, and subsequently, analysis of each fraction for a second property is carried out in parallel.

4. A process as claimed in claim 1, wherein all analyses of step (iii) are performed in parallel.

5. A process as claimed in claim 1, wherein the refinery feedstocks are selected from a crude oil, a synthetic crude, a biocomponent, an intermediate stream, and blends of one or more of said components.

6. A process as claimed in claim 1, wherein step (ii) comprises blending a refinery feedstock with one or more other refinery feedstocks.

7. A process as claimed in claim 1, wherein the plurality of fractions produced in step (ii) comprises at least 7 such fractions.

8. A process as claimed in claim 1, wherein the chemical and/or physical properties of the fraction which it is desired to analyse in step (iii) are selected from the group consisting of density, specific gravity, total acid number, total base number, cold flow properties, viscosity, hydrocarbon speciation, sulphur content, sulphur compounds speciation, nitrogen content, nickel content, vanadium content, acid speciation, asphaltine content, carbon content, metal content, micro carbon residue, chloride, and combinations thereof.

9. A process as claimed in claim 1, wherein the properties of the fractions which are analysed include one or more chemical properties.

10. A process as claimed in claim 1, wherein the evaluation is enhanced by performing further experiments repeating steps (ii) and (iii).

11. A process as claimed in claim 1, wherein the process is performed in a continuous manner.

12. A process as claimed in claim 1, wherein the process is repeated for analysis of different physical and/or chemical properties of the fractions.

13. A process as claimed in claim 1, wherein evaluation of process streams is "linked", such that a refinery feedstock is evaluated by analysis of two or more pluralities of different process streams.

14. A process as claimed in claim 1, wherein at least 5 process streams are evaluated in a "linked" way to provide information on the optimum refinery configuration for a particular feedstock.

15. A process as claimed in claim 1 which comprises the further step:

(iv) applying a refinery process model to determine the impact of the chemical and/or physical properties of the fractions on the subsequent processing of the fraction/process stream or on the overall processing of the refinery feedstock.

16. A process as claimed in claim 1 in which the data generated on the effect of refinery feedstocks on refinery process streams is utilised to develop, update, maintain and/or verify process models for one or more refinery processes.

17. A process according to claim 1, in which the array of refinery feedstocks is fractionated to produce a further array comprising a plurality of fractions having different chemical and/or physical properties at a rate of at least 50 refinery feedstocks per week, which process comprises the additional step of determining a value of each of said plurality of refinery feedstocks in said array.

18. The method of claim 17, wherein the determining step comprises: comparing said one or more chemical and/or physical properties to the price of refinery feedstocks having such one or more properties; identifying a processing facility for at least one of said plurality of refinery feedstocks based on the analyzing step; identifying a configuration of processing equipment for at least one of said plurality of refinery feedstocks based on the analyzing step; and/or identifying a material to blend with at least one of said plurality of refinery feedstocks based on the analyzing step.

19. A process as claimed in claim 5, wherein the intermediate stream is selected from a residue, gas oil, vacuum gas oil, naphtha or cracked stock.

20. A process as claimed in claim 1, wherein step (ii) further comprises treating a refinery feedstock using solvent extraction, membrane treatments, adsorption treatments and/or suitable chemical reactions.

* * * * *